(12) United States Patent
Kobayashi et al.

(10) Patent No.: US 6,790,189 B2
(45) Date of Patent: Sep. 14, 2004

(54) ERECTION SUPPORT RING

(75) Inventors: Katsuyoshi Kobayashi, Osaka (JP); Yasuo Morifuji, Osaka (JP)

(73) Assignee: Jex Co., Ltd. (JP)

( * ) Notice: Subject to any disclaimer, the term of this patent is extended or adjusted under 35 U.S.C. 154(b) by 0 days.

(21) Appl. No.: 10/209,533

(22) Filed: Jul. 31, 2002

(65) Prior Publication Data

US 2003/0083598 A1 May 1, 2003

(30) Foreign Application Priority Data

Oct. 31, 2001 (JP) ........................................ 2001-334884

(51) Int. Cl.[7] ............................................ A61M 11/00
(52) U.S. Cl. .............................. 601/70; 601/71; 600/38
(58) Field of Search ........................ 601/56–60, 67–74, 601/81–84, 46, 80, 79

(56) References Cited

U.S. PATENT DOCUMENTS

| | | | |
|---|---|---|---|
| 3,623,481 A | * | 11/1971 | Curran .......................... 601/74 |
| 5,397,294 A | * | 3/1995 | Hwang .......................... 601/71 |
| 6,338,721 B1 | * | 1/2002 | Lebecque ...................... 601/71 |
| 2002/0103415 A1 | * | 8/2002 | Manska et al. ............... 600/38 |
| 2002/0188235 A1 | * | 12/2002 | Manska ......................... 601/70 |

* cited by examiner

Primary Examiner—Jerome W. Donnelly
(74) Attorney, Agent, or Firm—Thompson Hine LLP

(57) ABSTRACT

An erection support ring includes a ring body, fabricated of soft rubber such as copolymerized rubber, swollen elastomer, or silicone rubber, and having an insert hole that elastically constricts a penis, and a cavity into which a small vibrator is removably placed. The ring body has a projection integrally formed therewith projecting in a direction in parallel with the center axis of the insert hole of the ring body. The small vibrator housed in the cavity vibrates, thereby providing stimulation at a comfortable level to the penis, leading the penis to erection, maintaining the erection of the penis, and finally inducing the penis to ejaculation. The vibration of the small vibrator is transferred to female sexual organs, thereby contributing to enhancing sexually pleasurable sensation to both of the male and the female.

6 Claims, 2 Drawing Sheets

(a)

(b)

ERECTION SUPPORT RING

BACKGROUND OF THE INVENTION

1. Field of the Invention

The present invention relates to improvements in the penis erection support ring that assists a penile function when mounted on a penis of a male during sexual intercourse.

2. Description of the Related Art

Problems of sexual complex due to a drop in the ability to achieve erection and unsuccessful sexual intercourse with a partner have been addressed, and a diversity of devices and medicines to remedy or improve the problems has been proposed and developed. The present invention relates to a penis constriction ring that continuously allows a penis to erect by constricting veins of a penis and occluding the circulation of blood through the penis when this support ring is mounted on the penis.

Drop in the ability to achieve erection or unsatisfied erection results from a variety of causes and this weak erection takes a variety of symptoms. If the penis of an individual is unable to erect because of his mental or physical disorder, a vacuum device or a medicine is used to force the penis to erect rather than using the ring during sexual intercourse. The drop in the erection ability results from not only the mental or physical disorder but also a drop in physical fitness with age, stress accumulated with fatigue or unresponsiveness to repeating of monotonous sexual acts. Majority of males who have a weak erection problem has daily life causes. Typically, these males do not attempt to use a large-scale device at each sexual intercourse, and avoid using a drug which could have a side effect. Although being aware of the weak erection, these males do not try a correct step, do not talk about the problem with a female partner, and some avoid entirely sexual acts themselves. It is a long time since this problem drew public attention. There has been a need for a male physical aid that is easily accepted by a partner and is simple in structure and is easy to use.

Although conventional penis constriction rings impose no load to both a male and a female, and easy to use, the rings themselves fail to induce erection and ejaculation of the penis. The rings are formed to assure sexual sensation to males during use, but no sufficient consideration is given to females.

SUMMARY OF THE INVENTION

Accordingly, it is an object of the present invention to provide an erection support ring that is easy to use, induces erection of the penis, and provides a sexually pleasurable sensation to a female as well.

To achieve the above object, an erection support ring of the present invention includes a ring body having an insert hole through which a penis inserted and elastically constricted, and a cavity into which a small vibrator is detachably housed. The ring of this invention occludes the flow of the blood in the penis to maintain the erection state thereof. This basic effect remains unchanged from that of the conventional ring. Besides the basic effect, the present invention applies an appropriate vibration to the penis with the small vibrator housed in the cavity of the ring body. This stimulation applied by the vibrator drives the penis to an erection state, maintains the erection state, and then induces ejaculation from the penis. During sexual intercourse, the vibration of the vibrator is transferred to a female, thereby providing a sexually pleasurable sensation to both a male and a female. Since the small vibrator is detachably housed in the ring, the vibrator may or may not be used, and a battery is replaced.

Preferably, the erection support ring includes a projection which is fabricated of the same material as the ring and integrally formed with the ring body. The projection is aligned in parallel with the direction of the center axis of the insert hole that is opened in the ring body, and is thus aligned with the longitudinal direction of the penis. The projection may be arranged on one side of the ring body, or may be arranged on both sides of the ring body. The projection mainly stimulates the sexual organs of a female. With the vibrator operating, the projection vibrates in a small-amplitude vibration. Preferably, the projection is formed in a location corresponding to the cavity. The projection is thus reliably vibrated. The arrangement in which the small vibrator is not housed in the cavity also falls within the scope of the present invention. In this arrangement, however, the projection becomes flexible with the cavity, thereby presenting a soft touch to the sexual organs.

Preferably, the mounting hole of the small vibrator has a smaller diameter than that of the cavity. In this arrangement, the small vibrator is almost entirely covered and is thus housed in an elastically sealed state. A body fluid is thus prevented from entering the cavity to assure hygiene. The vibrator is kept out of direct touch with the skin. The vibration of the vibrator is indirectly transferred to each sexual organs through an elastic member of the ring body and the projection. The applied stimulation becomes appropriate in level.

Preferably, the ring body is fabricated of an elastic material that is soft and elastic. This arrangement eliminates the sense of discomfort due to mounting and touch of the ring, and increases the user's satisfaction. The ring is fabricated of a material, such as natural rubber or synthetic rubber, elastic enough to be mounted on the penis and having no adverse effects on the human body. Specifically, the ring may be fabricated of copolymerized rubber, swollen elastomer, silicone rubber, or the like.

DESCRIPTION OF THE PREFERRED EMBODIMENTS

Figure 1:
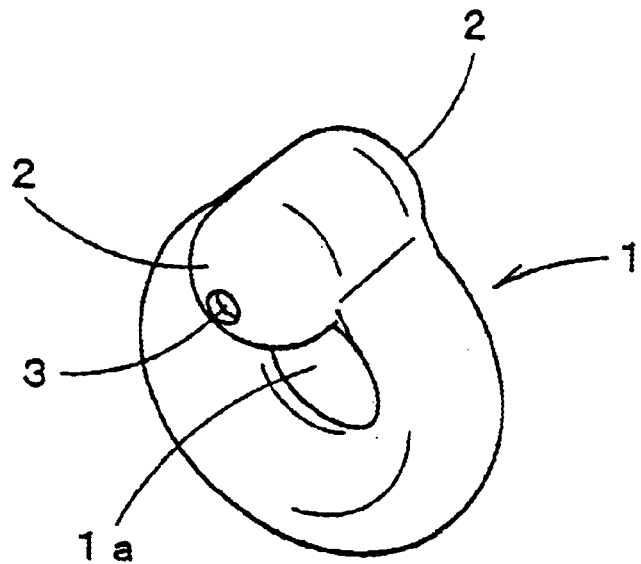
FIG. 1 is a perspective view of a male sexual ring in accordance with one embodiment of the present invention.

Preferred embodiments of the present invention will now be discussed with reference to the drawings. FIG. 1 is a perspective view of a male sexual ring in accordance with one preferred embodiment of the present invention. As shown, a ring body 1 has an insert hole 1a, and a projection 2 is arranged on the top portion of the ring. The projection 2 projects in a fore-aft direction in parallel with the direction of the center axis of the insert hole 1a. The projection 2 and the ring body 1 are integrally fabricated of Polyethylene (hereinafter PE) elastomer. The material thereof is not limited to PE elastomer. Any material such as silicone rubber may be molded into the ring as long as it is elastic and mountable on the penis. To improve comfort with which the user feels, the material of the ring is preferably soft and elastic. In this embodiment, the ring body 1 is 40 mm in outer diameter, and 12 mm thick before mounting. The insert hole 1a has a diameter of 20 mm. The projection 2 has a diameter of 18 mm, and has a total length of 28 mm. The size, however, is not limited as above and be able to be arranged depends on user's size.

Figure 2:
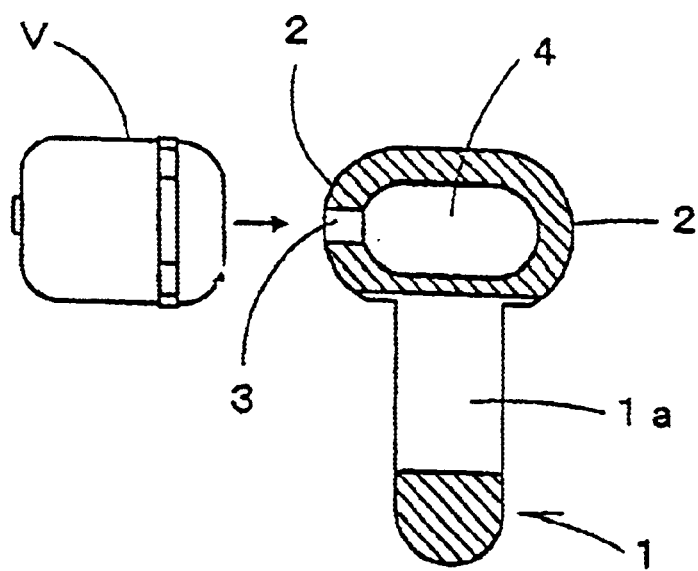
FIG. 2 is a cross-sectional view of the male sexual ring.

A mounting hole 3 is formed in one end face of the projection 2, and communicates with a cavity 4 that is formed by cutting away a portion of the projection 2 and a portion of the ring body 1 where the projection 2 is arranged as shown in FIG. 2.

The cavity 4 may house a small vibrator V, for example. The vibrator V is inserted into the cavity 4 through the mounting hole 3. In this embodiment, a cordless type miniature vibrator having a diameter of about 20 mm and a total length of about 23 mm is used. The cavity 4 is sized to be about four times smaller than the vibrator V The vibrator V is thus tightly housed in the cavity 4. The mounting hole 3 of the vibrator V has a diameter of about 8 mm, substantially smaller than that of the cavity 4. The diameter of the mounting hole 3 is preferably set to be the smallest possible one through which the vibrator V is loaded and unloaded with elasticity. The vibrator V is almost entirely closed within the cavity 4, and body fluid doesn't enter the cavity 4, and hygiene of the vibrator is thus assured.

The method of mounting the ring of this embodiment remains unchanged from the conventional constriction ring. Using fingers or a dedicated mounting device, the insert hole 1a is enlarged against elasticity and mounted around the base portion of the penis. During mounting, the ring of the present invention does not require that the penis be erected. The ring may be mounted around the penis in the flaccid state thereof. In this case, the penis is induced into the tumescent state thereof as will be discussed later.

The method of using the ring of the present invention is discussed below. When the penis is already in the erect state or tumescent state with the ring mounted, the ring body 1 constricts a root portion of the penis, and blocks the circulation of the blood in the penis with the veins thereof occluded. The penis is thus kept erected. When the ring is mounted prior to the tumescent state, the vibrator V housed in the cavity 4 is activated. The fine vibration of the vibrator V is applied, thereby stimulating the penis to the tumescent state thereof. The vibrator V is entirely covered with the elastic member so that the vibrator V is not directly put into contact with the penis. The vibration of the vibrator V vibrates the entire ring, thereby becoming a comfortable stimulation to the penis.

With the penis reaching the tumescent state, the fine vibration of the vibrator V stimulates the penis, thereby keeping the penis erected in cooperation with the constriction effect of the ring body 1. Even if the blood is circulated for some reason, the fine vibration of the vibrator V reinforces the penis in the tumescent state thereof, thereby preventing the penis from losing its erection in the middle of sexual intercourse. The vibrator V vibrating in fine amplitude induces the male to ejaculation.

The projection 2 projecting from the ring body 1 is put into contact with the female sexual organs during intercourse, thereby stimulating her. With the vibrator V operating, the stimulation level is heightened. The vibrator V may be switched off if no vibration is desired. The position of the projection 2 is changed depending on the mounting position of the ring. If the vibrator V is not placed into the cavity 4, the projection 2 becomes more flexible, thereby more softly touching the female sexual organs. The cavity 4 not only accommodates the vibrator V but also adjusts the softness with which the projection 2 is put into contact with the female sexual organs.

Figure 3:
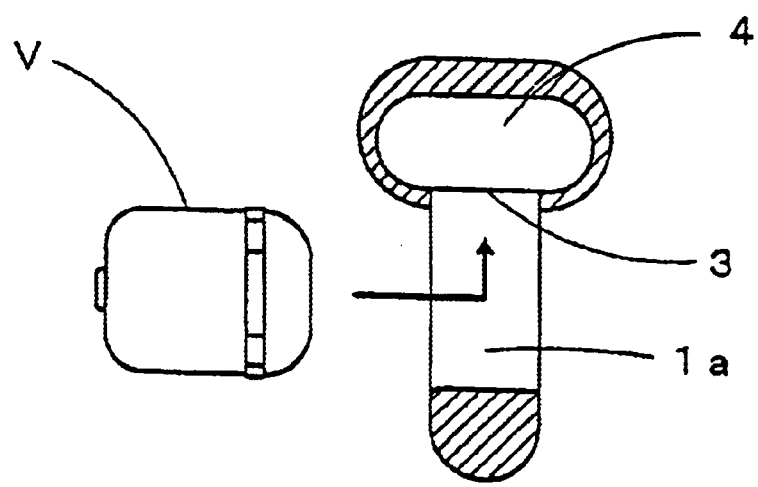
FIGS. 3A and 3B are cross-sectional views of the ring in accordance with another embodiment of the present invention.
Figure 3:
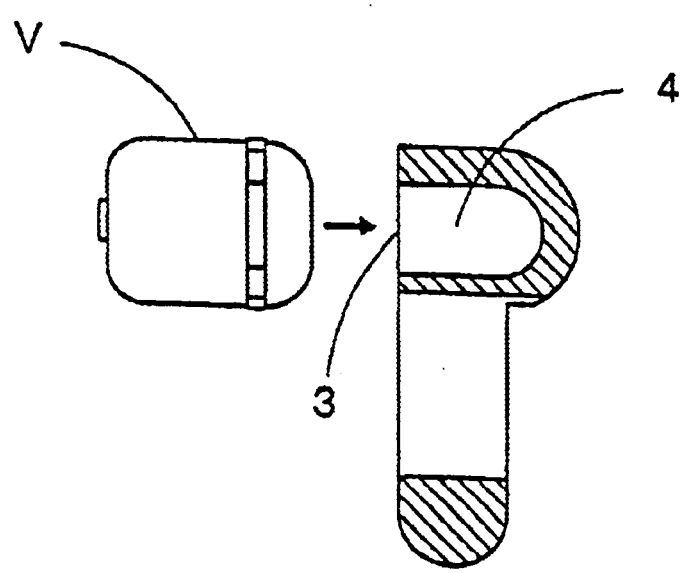

The mounting hole 3 is preferably arranged on the end of the projection 2 as described above so that the vibrator V is entirely covered with the elastic member to set the vibration to a comfortable level. Alternatively, however, the mounting hole 3 may be opened in the wall of the insert hole 1a of the ring body 1 as shown in FIG. 3A. The projection 2 may be arranged on one side of the ring body 1 and the mounting hole 3 is opened on one end of the projection 2 as shown in FIG. 3B.

As described above, the erection of the penis is assisted by the constriction effect of the ring body 1, and the projection 2 results in a sexually pleasurable sensation to the female. The cavity of the projection 2 is used to adjust the softness with which the projection is put into contact with the female. When the small vibrator is placed into the cavity, the vibration of the vibrator becomes a stimulant to the male, thereby stimulating the penis, inducing and maintaining the tumescent state in the penis, and finally leading the male to ejaculation. The ring also enhances the sexually pleasurable sensation in the female.

What is claimed is:

1. An erection support ring comprising:
    an elastic ring body having an insert hole through which a penis is insertable and elastically constricted;
    a vibrator, and;
    an elastic deformable projection which projects in a direction in parallel with the direction of the center axis of the insert hole and is integrally formed with the ring body, wherein a cavity into which said vibrator is detachably housed, is formed in the projection and a mounting hole which is formed in a face of the projection, through which said vibrator is inserted into said cavity.

2. An erection support ring according to claim 1, the mounting hole being in communication with the cavity for mounting the small vibrator in the cavity.

3. An erection support ring according to claim 1, wherein the ring body is fabricated of an elastic material that is soft and elastic.

4. An erection support ring according to claim 3, wherein the elastic material is copolymerized rubber.

5. An erection support ring according to claim 3, wherein the elastic material is swollen elastomer.

6. An erection support ring according to claim 3, wherein the elastic material is silicone rubber.

* * * * *